United States Patent [19]

Preston et al.

[11] 4,027,023

[45] May 31, 1977

[54] CINNOLIN-3-YL CARBOXYLIC ACIDS AND DERIVATIVES

[75] Inventors: John Preston; Michael John Cooper, both of Macclesfield, England

[73] Assignee: Imperial Chemical Industries Limited, London, England

[22] Filed: July 28, 1975

[21] Appl. No.: 599,348

[30] Foreign Application Priority Data

Aug. 19, 1974 United Kingdom ............. 36360/74

[52] U.S. Cl. ............................ 424/250; 260/250 C
[51] Int. Cl.$^2$ ................ C07D 231/28; A61K 31/50
[58] Field of Search ................. 424/250; 260/250 C

[56] References Cited

UNITED STATES PATENTS 3,657,241  4/1972  Kurihara ........................ 260/250 C

OTHER PUBLICATIONS

Baumgarten et al., J.A.C.S. 80, 1980 (1958).
Haas et al., Chem. Abs. 60, 9344h (1964).

*Primary Examiner*—Donald G. Daus
*Assistant Examiner*—Mark L. Berch
*Attorney, Agent, or Firm*—Cushman, Darby & Cushman

[57] ABSTRACT

Cinnolin-3-yl carboxylic acids and esters, amides and like derivatives, processes for the preparation of these compounds, and pharmaceutical compositions comprising any one of these compounds. A representative compound is ethyl 6-ethylcinnolin-3-yl carboxylate. The compounds are active as inhibitors of effects following the combination of reagin-like antibodies and their antigens.

7 Claims, No Drawings

CINNOLIN-3-YL CARBOXYLIC ACIDS AND DERIVATIVES

This invention relates to heterocyclic compounds and more particularly it relates to cinnoline derivatives which are active as inhibitors of the effects following the combination of reagin-like antibodies and their antigens.

According to the invention there are provided compounds of the formula:

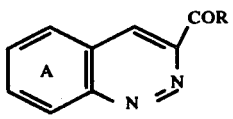

wherein R stands for a hydroxy, $C_{1-6}$-alkoxy, $C_{3-6}$-alkoxyalkoxy, $C_{4-10}$-dialkylaminoalkoxy, $C_{7-10}$-phenylalkoxy, phenoxy, amino, hydrazino, hydroxyamino, ($C_{1-4}$-alkoxy)carbonylmethylamino or 1,2,3,4-tetrazol-5-ylamino radical, and the benzene ring A may optionally bear one or two substituents selected from $C_{1-5}$-alkyl, $C_{5-7}$-cycloalkyl, $C_{1-3}$-alkoxy, benzyl, amino, $C_{1-4}$-alkylamino, $C_{2-5}$-alkanoylamino and benzyloxycarbonylamino radicals, and nitro groups and halogen atoms, and phenyl radicals which themselves may optionally bear one or two substituents selected from $C_{1-3}$-alkoxy radicals and nitro groups and halogen atoms, and pharmaceutically-acceptable salts thereof, but excluding cinnolin-3-yl carboxylic acid and its ethyl ester, ethyl 6-chlorocinnolin-3-yl carboxylate and ethyl 7-chlorocinnolin-3-yl carboxylate, and pharmaceutically-acceptable salts thereof.

A suitable value for R is, for example, a hydroxy, methoxy, ethoxy, 2-ethoxyethoxy, 2-diethylaminoethoxy, phenoxy, benzyloxy, amino, hydrazino, hydroxyamino, methoxycarbonylmethylamino or 1,2,3,4-tetrazol-5-ylamino radical. The benzene ring A may optionally bear one or two substituents, which may be selected from, for example, methyl, ethyl, n-propyl, n-butyl, cyclohexyl, methoxy, benzyl, amino, isopropyamino, acetylamino and benzyloxycarbonylamino radicals, and nitro groups, and phenyl, methoxyphenyl, dinitrophenyl and chlorophenyl radicals, and fluorine, chlorine and bromine atoms.

According to one embodiment of the invention there are provided compounds of the formula I wherein R has the meaning stated immediately above and the benzene ring A optionally bears, for example in the 7,8-positions (relative to the cinnoline nucleus), two methyl radicals or it bears, for example in the 6-position (relative to the cinnoline nucleus), a methyl, ethyl, n-propyl, n-butyl, cyclohexyl, methoxy, benzyl, amino, isopropylamino, acetylamino or benzyloxycarbonylamino radical, or a nitro group, or a phenyl, methoxyphenyl, dinitrophenyl or chlorophenyl radical, or a chlorine or bromine atom, and pharmaceutically-acceptable salts thereof, but excluding cinnolin-3-yl carboxylic acid and its ethyl ester, ethyl 6-chlorocinnolin-3-yl carboxylate and ethyl 7-chlorocinnolin-3-yl carboxylate, and pharmaceutically-acceptable salts thereof.

According to a preferred embodiment of the invention there are provided compounds of the formula I wherein R stands for a hydroxy, methoxy, ethoxy, 2-diethylamino-ethoxy, phenoxy, hydroxyamino or 1,2,3,4-tetrazol-5-ylamino radical, and the benzene ring A bears in the 6-position (relative to the cinnoline nucleus) an ethyl, n-propyl, cyclohexyl, amino, acetylamino, phenyl, p-chlorophenyl or dinitrophenyl radical, or a chlorine or bromine atom, and pharmaceutically-acceptable salts thereof, but excluding ethyl 6-chlorocinnolin-3-yl carboxylate and pharmaceutically-acceptable salts thereof.

Preferred specific compounds of the invention are 6-bromocinnolin-3-yl carboxylic acid and 6-phenylcinnolin-3-yl carboxylic acid and pharmaceutically-acceptable salts thereof.

Suitable salts of the invention are, in the case where the compound of the formula I is sufficiently basic, pharmaceutically-acceptable acid-addition salts derived from inorganic or organic acids. Examples are hydrochlorides, hydrobromides, tartrates and citrates. Suitable salts in the case where the said compound of the formula I are sufficiently acidic are salts in which the anionic part is derived from the compound of the formula I and the cationic part is a pharmaceutically-acceptable cation. Examples are ammonium salts, alkali metal salts, alkaline earth metal salts, aluminium salts and salts with pharmaceutically-acceptable organic bases, for example N-methylglucamine, triethanolamine or 2-amino-2-hydroxymethyl-1,3-propanediol.

The compounds of the invention are obtainable by analogy processes, and these features of the invention will now be described.

According to a further feature of the invention there is provided a process for the manufacture of compounds of the formula I, wherein R and A have the meanings stated above, and pharmaceutically-acceptable salts thereof, which comprises oxidising a compound of the formula:

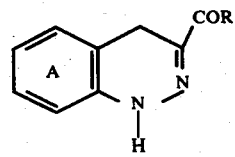

wherein R and A have the meanings stated above, so as to aromatise the dihydropyridazine ring.

Suitable oxidising agents are, for example, lead tetraacetate, manganese dioxide, 2,3-dichloro-5,6-dicyano-1,4-benzoquinone and diethyl azodicarboxylate. An alternative oxidising agent is oxygen, optionally in the presence of an oxygenation catalyst. The reaction may be carried out in an organic solvent, for example a lower alkyl lower alkanoate of up to 8 carbon atoms, for example ethyl acetate, or an aromatic hydrocarbon, for example toluene. The reaction may optionally be carried out at a moderately elevated temperature, for example under reflux.

The starting materials of the formula II may be obtained as follows:

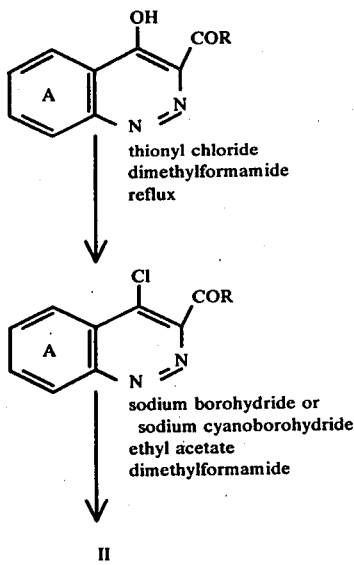

for example, as described in detail in Example 1.

According to a further feature of the invention there is provided a process for the manufacture of compounds of the formula I wherein R stands for a hydroxy radical and A has the meaning stated above, and pharmaceutically-acceptable salts thereof, which comprises hydrolysing a compound of the formula:

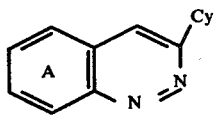

wherein A has the meaning stated above and Cy stands for an alkoxycarbonyl, phenylalkoxycarbonyl, phenoxycarbonyl, cyano, carbamoyl or thiocarbamoyl radical.

The hydrolysis is carried out in the presence of water, and optionally an organic solvent, for example ethanol, may also be present. A suitable hydrolytic agent is, for example, an alkali metal hydroxide, for example sodium hydroxide, or an inorganic acid, for example hydrochloric acid. The reaction may optionally be carried out at a moderately elevated temperature, for example at approximately 100° C.

The esters of the formula V used as starting materials may be obtained by processes described herein, and the other starting materials of the formula V may be obtained by known general synthetic procedures.

According to a further feature of the invention there is provided a process for the manufacture of those of the compounds of the formula I wherein R has the meaning stated above and the benzene ring A bears one or two amino radicals, and pharmaceutically-acceptable salts thereof, which comprises catalytically hydrogenating the corresponding compound wherein the benzene ring A bears one or two nitro groups.

A suitable hydrogenation catalyst is, for example, palladium on charcoal. The hydrogenation may be carried out in a suitable organic solvent, for example a $C_{1-4}$-alkanol, for example ethanol.

According to a further feature of the invention there is provided a process for the manufacture of those of the compounds of the formula I wherein A has the meaning stated above and R stands for an amino, hydrazino, hydroxyamino, $(C_{1-4}$-alkoxy)carbonylmethylamino or 1,2,3,4-tetrazol-5-ylamino radical, and pharmaceutically-acceptable salts thereof, which comprises reacting a corresponding acid halide with a compound of the formula RH, wherein R has the meaning stated immediately above.

A suitable acid halide is, for example, the acid chloride, and these are obtainable in conventional manner from the corresponding acid. The reaction involving an acid halide may be carried out in a suitable organic solvent, for example pyridine or methylene chloride (in the presence of triethylamine).

According to a further feature of the invention there is provided a process for the manufacture of those of the compounds of the formula I wherein R has the meaning stated above and the benzene ring A bears one or two $C_{2-5}$-alkanoylamino radicals, and pharmaceutically-acceptable salts thereof, which comprises acylating a corresponding compound wherein the benzene ring A bears one or two amino radicals.

A suitable acylating agent is, for example, an acid halide or acid anhydride derived from an $C_{2-5}$-alkanoic acid. The reaction may optionally be carried out in the presence of a suitable organic solvent, for example pyridine, and it may be carried out at a moderately elevated temperature, for example at 100° C.

According to a further feature of the invention there is provided a process for the manufacture of those of the compounds of the formula I wherein A has the meaning stated above and R stands for an amino, hydrazino, hydroxyamino or $(C_{1-4}$-alkoxy)carbonylmethylamino radical, and pharmaceutically-acceptable salts thereof, which comprises reacting a corresponding ester, wherein R stands for a $C_{1-6}$-alkoxy radical, with ammonia, hydrazine, hydroxylamine or a $(C_{1-4}$-alkoxy)carbonylmethylamine.

The reaction is conveniently carried out in the presence of a suitable organic solvent, for example a dry $(C_{1-3}$-alkanol), for example ethanol.

According to a further feature of the invention there is provided a process for the manufacture of those of the compounds of the formula I wherein R has the meaning stated above and the benzene ring A bears a nitrophenyl or dinitrophenyl radical, and pharmaceutically-acceptable salts thereof, which comprises nitrating a corresponding compound wherein the benzene ring A bears an unsubstituted phenyl radical.

The nitration may be carried out by means of, for example, concentrated nitric acid and concentrated sulphuric acid under reflux.

According to a further feature of the invention there is provided a process for the manufacture of those of the compounds of the formula I wherein A has the meaning stated above and R stands for a $C_{1-6}$-alkoxy, $C_{3-6}$-alkoxyalkoxy, $C_{4-10}$-dialkylaminoalkoxy, $C_{7-10}$-phenylalkoxy or phenoxy radical, and pharmaceutically-acceptable salts thereof, which comprises esterifying a corresponding acid.

The esterification may be carried out in conventional manner; for example, an acid anhydride or an acid halide, for example an acid chloride, may be reacted with the appropriate alcohol (RH) in a suitable organic solvent, for example dry tetrahydrofuran. The reaction may be carried out at a moderately elevated temperature, for example under reflux.

According to a further feature of the invention there is provided a process for the manufacture of those of the compounds of the formula I wherein R has the meaning stated above and the benzene ring A bears one or two $C_{1-4}$-alkylamino radicals, and pharmaceutically-acceptable salts thereof, which comprises reacting a corresponding compound, in which the benzene ring A bears one or two amino radicals, with an aldehyde or ketone of the formula $R^1COR^2$, wherein $R^1$ stands for an alkyl radical, and $R^2$ stands for hydrogen or alkyl radical, and provided that $R^1COR^2$ does not contain more than four carbon atoms, either in the presence of hydrogen and a hydrogenation catalyst, for example a platinum catalyst, or in the presence of an alkali metal borohydride or an alkali metal cyanoborohydride, for example sodium borohydride or sodium cyanoborohydride.

The above-mentioned reductive alkylation process may optionally be carried out in a suitable organic solvent, for example ethanol.

The above-mentioned activity of the compounds of the invention has been demonstrated by their ability to inhibit, in the rat, passive cutaneous anaphylaxis induced by reagin-like antibodies to egg albumin, using *Bordetella pertussis* as an adjuvant. The activity of individual compounds of the invention in this test depends upon their precise chemical structure, but generally speaking the compounds exhibit activity at a dose of 0.2 to 20 mg./kg. No toxic effects or other undesirable effects have been observed with the compounds at doses at which they are active in the above-mentioned test. One particularly important feature of the compounds of the invention is that they are active inter alia orally.

When a compound of the invention is used in a warm-blooded mammal, for example man, for the treatment of intrinsic (non-allergic) asthma or of a disease or syndrome which is initiated by an antigen-antibody reaction, for example allergic asthma, hay fever, urticaria or an autoimmune disease, it is recommended that said compound is administered either 1. orally at a dose of 5 mg. to 250 mg. per man at suitable intervals, for example at 6-hourly intervals during the day; or
2. by inhalation at a dose of 0.01 mg./kg. to 1 mg./kg. at suitable intervals, for example at 6-hourly intervals during the day;
3. intravenously at a total daily dose of 10 to 100 mg. per man; or
4. as a suppository at a dose of 5 to 250 mg.

According to a further feature of the invention there are provided pharmaceutical compositions comprising a compound of the formula I, wherein R stands for a hydroxy, $C_{1-6}$-alkoxy, $C_{3-6}$-alkoxyalkoxy, $C_{4-10}$-dialkylaminoalkoxy, $C_{7-10}$-phenylalkoxy, phenoxy, amino, hydrazino, hydroxyamino, ($C_{1-4}$-alkoxy)carbonylmethylamino or 1,2,3,4-tetrazol-5-ylamino radical, and the benzene ring A may optionally bear one or two substituents selected from $C_{1-5}$-alkyl, $C_{5-7}$-cycloalkyl, $C_{1-3}$-alkoxy, benzyl, amino, $C_{1-4}$-alkylamino, $C_{2-5}$-alkanoylamino and benzyloxycarbonylamino radicals and nitro groups and halogen atoms, and phenyl radicals which themselves may optionally bear one or two substituents selected from $C_{1-3}$-alkoxy radicals and nitro groups and halogen atoms, or a pharmaceutically-acceptable salt thereof, and an inert pharmaceutically-acceptable diluent or carrier.

The compositions of the invention are all obtainable by conventional methods using conventional excipients. The compositions may be in the form of an orally-administrable unit dosage form, for example a tablet or capsule, and more particularly a tablet containing 5 to 50 mg. of the cinnoline derivative of the invention. Alternatively, they may be in a form adapted for administration by inhalation, for example a solution or suspension in an aqueous or non-aqueous medium, which is administered by inhalation using a conventional nebulizer or a pressurised container, for example an aerosol dispenser, for example a breath-actuated aerosol dispenser. Alternatively, the compositions may comprise a mixture of the active ingredient with a solid diluent or carrier, for example lactose, the said mixture being in a fine particulate form suitable for administration by inhalation using a powder inhalation device. Alternatively, the compositions may be in a form adapted for intravenous administration, for example a sterile solution or suspension. Alternatively, the compositions may be in the form of a suppository.

The pharmaceutical compositions of the invention may contain, in addition to a cinnoline derivative which characterises this invention, one or more of the following known compounds:

a. compounds which are known to be useful in the treatment of asthma and which are selected from:
   i. bronchodilators, for example atropine or a β-adrenergic stimulant, for example isoprenaline, adrenaline, salbutamol, orciprenaline or isoethacine;
   ii. corticosteroids, for example beclomethasone dipropionate or betamethasone valerate; and
   iii. phosphodiesterase inhibitors for example theophylline or aminophylline; and
b. i. α-adrenergic blocking agents, for example phentolamine;
   ii. prostaglandin $E_1$ or $E_2$;
   iii. 3-acetamido-6-methyl-8-n-propyl-s-triazolo[4,3-a]pyrazine;
   iv. 2-amino-4,6-di-$C_{1-4}$-alkyl-5-oxo-4,5-dihydro-s-triazolo[1,5-a]pyrimidines; and
   v. 6,8-di-$C_{1-4}$-alkyl-5,6-dihydro-5-oxo-s-triazolo[4,3-c]pyrimidines.

The pharmaceutical compositions of the invention may contain from 1 to 50% by weight of a compound of the formula I or a pharmaceutically-acceptable salt thereof.

The invention is illustrated but not limited by the following Examples:

EXAMPLES 1–3

Example 1

Lead tetraacetate (13 g.) was added to a stirred solution of ethyl 6-ethyl-1,4-dihydrocinnolin-3-yl carboxylate (4.25 g.) in ethyl acetate (400 ml.). The suspension was stirred at room temperature for 2 hours, and then shaken with water (400 ml.) and the mixture separated. The ethyl acetate layer was washed with water (3 × 200 ml.), dried (MgSO$_4$), and filtered. The filtrate was evaporated to ca. 20 ml. and petroleum ether (b.p. 40°–60° C., ca. 50 ml.) was added. The resulting mixture was filtered and there was thus obtained ethyl 6-ethylcinnolin-3-yl carboxylate, m.p. 71°–3° C.

The ethyl ester used as starting material was obtained as follows:

To ethyl 6-ethyl-4-hydroxycinnolin-3-yl carboxylate (1.23 g.) was added thionyl chloride (35 nl.) and dimethylformamide (1 drop). The mixture was gradually warmed to boiling and was then boiled under reflux until gaseous evolution ceased. The solution was evaporated under reduced pressure. The residue was dissolved in dry toluene (20 ml.) and evaporated, and the residue was again dissolved in dry toluene (20 ml.) and the solution evaporated. The residual solid (ethyl 4-chloro-6-ethylcinnolin-3-yl carboxylate) was dissolved in a mixture of dimethylformamide (10 ml.) and ethyl acetate (25 ml.). The resulting solution was stirred and sodium borohydride (0.76 g.) was added. The mixture was stirred for 2 hours and was then added to a mixture of N-hydrochloric acid (30 ml.) and ethyl acetate (150 ml.), and the mixture separated. The ethyl acetate layer was washed with water (3 × 50 ml.), dried ($MgSO_4$), and filtered. The filtrate was evaporated under reduced pressure to a smaller volume. The addition of petroleum ether (b.p. 40°–60° C.) caused crystalline ethyl 6-ethyl-1,4-dihydrocinnolin-3-yl carboxylate, m.p. 171°–3° C., to separate.

In a similar manner to that described above in respect of ethyl 6-ethylcinnolin-3-yl carboxylate, and using the appropriate starting materials, the following compounds were obtained:

Example 2

Ethyl 6-n-butylcinnolin-3-yl carboxylate, $R_F$ = 0.55 on thin layer chromatography on silica (Kieselgel GF 254; E. Merck, Darmstadt) using ether as the eluent; and

Example 3

Ethyl 6-p-chlorophenylcinnolin-3yl carboxylate, m.p. 150°–2° C. The atarting materials used in the preparation of these two compounds, viz. ethyl 6-n-butyl-1,4-dihydrocinnolin-3-yl carboxylate (m.p. 150°–152° C.) and ethyl 6-p-chlorophenyl-1,4-dihydrocinnolin-3-yl carboxylate (m.p. 254°–256° C.), were obtained in a similar manner to that described above for the preparation of ethyl 6-ethyl-1,4-dihydrocinnolin-3-yl carboxylate.

Ethyl 6-p-chlorophenyl-4-hydroxycinnolin-3-yl carboxylate, which was used as starting material in the preparation of the last-named chlorophenyl derivative, was obtained as follows:

Dry ethanol (250 ml.) was stirred and cooled at -40° C. as thionyl chloride (35 ml.) was added dropwise. When the addition was complete the solution was stirred for 10 minutes at -40° C. 6-p-Chlorophenyl-4-hydroxycinnolin-3-yl carboxylic acid (4.5 g.) was added to the stirred solution at −40° C. Stirring was continued and the mixture was allowed to warm up to room temperature overnight. The mixture was then heated under reflux for 1 hour, allowed to cool, filtered, and the filtrate evaporated to dryness under reduced pressure. The solid residue was recrystallised from a mixture of ethyl acetate and petroleum ether (b.p. 60°–80° C.) and had m.p. 259°–261° C.

EXAMPLE 4

N-Sodium hydroxide (10 ml.) was added to a stirred solution of ethyl 6-ethylcinnolin-3-yl carboxylate (2.3 g.) in ethanol (10 ml.). The mixture was stirred at room temperature overnight. It was then evaporated under reduced pressure to approximately half-volume, diluted with water (20 ml.), and the mixture filtered. The filtrate was cooled to 0°–5° C., and acidified to pH 2 with concentrated hydrochloric acid. The resulting precipitate was filtered off, washed with water, and dried in vacuo. The solid was crystallised from a mixture of ethyl acetate and petroleum ether (b.p. 40°–60° C.) to give 6-ethylcinnolin-3-yl carboxylic acid, m.p. 176°–8° C. (decomposition).

EXAMPLE 5

6-n-Butylcinnolin-3-yl carboxylic acid (m.p. 131°–3° C.) was obtained from the corresponding 6-n-butyl derivative in a similar manner to that described in Example 4.

EXAMPLE 6

Thionyl chloride (15 ml.) and dimethylformamide (1 drop) were added to ethyl 4-hydroxy-6-phenylcinnolin-3-yl carboxylate (0.30 g.). The mixture was gradually heated to boiling point and then heated under reflux until the evolution of gases ceased. The solution was evaporated under reduced pressure. The residue was dissolved in dry toluene (20 ml.) and the solution evaporated; this operation was then repeated. The residue was dissolved in a mixture of dimethylformamide (5 ml.) and ethyl acetate (30 ml.). The solution was stirred and sodium borohydride (0.25 g.) was added. The mixture was stirred for 2 hours and then added to a mixture of N-hydrochloric acid (10 ml.) and ethyl acetate (50 ml.). The mixture was separated and the ethyl acetate layer was washed with water (3 × 20 ml.), dried ($MgSO_4$), filtered, and the filtrate evaporated under reduced pressure. The residue (which comprised ethyl 6-phenyl-1,4-dihydrocinnolin-3-yl carboxylate) was dissolved in dry toluene (50 ml.). Lead tetraacetate (1 g.) was added, and the mixture was stirred for 2 hours. The mixture was shaken with water (50 ml.), and separated. The organic layer was washed with water (3 × 50 ml.), dried ($MgSO_4$), filtered, and the filtrate evaporated under reduced pressure. The residue was crystallised from a mixture of ethyl acetate and petroleum ether (b.p. 60°–80° C.) to give ethyl 6-phenylcinnolin-3-yl carboxylate, m.p. 160°–2° C.

EXAMPLES 7–9

Example 7

A mixture of cinnolin-3-yl carboxylic acid (5 g.), maize starch (65 g.), calcium phosphate (130 g.) and magnesium stearate (1 g.) was compressed, and the compressed mixture was then broken down into granules by passage through a 16-mesh screen (British Pharmacopoeia 1968, page 1373). The granules produced were then compressed into tablets each containing 50 mg. of the active ingredient.

In a similar manner tablets were obtained containing 50 mg. of either ethyl cinnolin-3-yl carboxylate (Example 8) or ethyl 6-chlorocinnolin-3-yl carboxylate (Example 9).

EXAMPLE 10

A solution of ethyl 6-bromo-1,4-dihydrocinnolin-3-yl carboxylate in ethyl acetate (obtained as described below) was heated to reflux temperature, and to it was added manganese dioxide (10 g.). The mixture was heated under reflux for 30 minutes and then filtered. The filtrate was evaporated to approx. 25 ml., and petroleum ether (b.p. 60°–80° C.) was added, causing crystalline ethyl 6-bromocinnolin-3-yl carboxylate (m.p. 151° C.) to separate out.

The solution used as starting material was obtained as follows:

Dry ethanol (50 ml.) was stirred and cooled at −40° C. as thionyl chloride (2 ml.) was added dropwise.

When addition was complete the solution was stirred for 10 minutes at −40° C. 6-Bromo-4-hydroxycinnolin-3-yl carboxylic acid (3.0 g.) was added to the stirred solution at −40° C. Stirring was continued and the mixture was allowed to warm up to room temperature overnight. The mixture was heated under reflux for 1 hour and then cooled in ice. The mixture was filtered and the solid residue washed with dry ethanol. There was thus obtained ethyl 6-bromo-4-hydroxycinnolin-3-yl carboxylate, m.p. 253° C.

To ethyl 6-bromo-4-hydroxycinnolin-3-yl carboxylate (3.0 g.) was added thionyl chloride (35 ml.) and dimethylformamide (1 drop). The mixture was gradually warmed to boiling point, and was then heated under reflux until gaseous evolution ceased. The solution was evaporated under reduced pressure. The residue was suspended in dry toluene (25 ml.) and evaporated. The residual solid (ethyl 6-bromo-4-chloro-cinnolin-3-yl carboxylate) was dissolved in a mixture of dimethylformamide (10 ml.) and ethyl acetate (90 ml.). The resulting solution was cooled to 0°-5° C. and stirred, and sodium borohydride (1.5 g.) was added. The mixture was stirred for 2 hours, and then added to a mixture of N-hydrochloric acid (100 ml.) and ethyl acetate (150 ml.). The layers were separated and the ethyl acetate layer was washed with water (2 × 100 ml.), dried (MgSO$_4$) and filtered.

EXAMPLES 11-15

In a similar manner to that described in Example 10, and using the appropriate starting materials, the following compounds were obtained:

| Example No. | Compound | m.p. (° C.) |
|---|---|---|
| 11 | ethyl 8-bromocinnolin-3-yl carboxylate | 116-8 |
| 12 | methyl 6-methoxycinnolin-3-yl carboxylate | 200-1 |
| 13 | ethyl 6-cyclohexylcinnolin-3-yl carboxylate | 86-8 |
| 14 | ethyl 7,8-dimethylcinnolin-3-yl carboxylate | 108-110 |
| 15 | ethyl 6-benzylcinnolin-3-yl carboxylate | 115 |

EXAMPLE 16

N-sodium hydroxide (50 ml.) was added to a stirred solution of ethyl 6-bromocinnolin-3-yl carboxylate (3.3. g.) in ethanol (20 ml.). The solution was boiled in the atmosphere to remove most of the ethanol, and then heated at 100° C. for 30 minutes. The mixture was then cooled to room temperature and acidified to pH 2 with concentrated hydrochloric acid. The resulting solid precipitate was filtered off and washed with water. The product, 6-bromocinnolin-3-yl carboxylic acid, was recrystallised from aqueous ethanol and had m.p. 203°-4° C.

EXAMPLE 17

6-Cyclohexylcinnolin-3-yl carboxylic acid, m.p. 159°-161° C., was obtained in a similar manner to that described in Example 16.

EXAMPLE 18

To a stirred solution of ethyl 6-phenylcinnolin-3-yl carboxylate (1.0 g.) in ethanol (15 ml.) was added N-sodium hydroxide (50 ml.). The solution was boiled in the atmosphere to remove most of the ethanol, and the heating was then continued at 100° C. for 30 minutes. The mixture was cooled to room temperature and acidifed to pH 2 with concentrated hydrochloric acid. The solid precipitate was washed with water and dried, and there was thus obtained 6-phenylcinnolin-3-yl carboxylic acid, m.p. 216°-8° C.

EXAMPLE 19

6-Chlorocinnolin-3-yl carboxylic acid, m.p. 207°-8° C., was obtained in a similar manner to that described in Example 18.

EXAMPLE 20

A solution of ethyl 6-nitro-1,4-dihydrocinnolin-3-yl carboxylate (obtained as described below) was heated to reflux temperature, and manganese dioxide (20 g.) was added. The mixture was heated under reflux for 30 minutes and then filtered. The filtrate was evaporated to a small volume (approx. 25 ml.), and petroleum ether (b.p. 60°-80° C.; 75 ml.) was added. The resulting mixture was filtered and there was thus obtained ethyl 6-nitrocinnolin-3-yl carboxylate, m.p. 154°-6° C.

The solution used as starting material was obtained as follows:

To ethyl 4-hydroxy-6-nitrocinnolin-3-yl carboxylate (3.0 g.) was added thionyl chloride (35 ml.) and dimethylformamide (1 drop). The mixture was gradually warmed to boiling and then heated under reflux until gaseous evolution ceased. The solution was evaporated under reduced pressure. The residue was suspended in dry toluene (25 ml.) and then evaporated. The residual solid (ethyl 4-chloro-6-nitro-cinnolin-3-yl carboxylate) was dissolved in a mixture of dimethylformamide (10 ml.) and ethyl acetate (90 ml.). The resulting solution was cooled to 0°-5° C. and stirred, and sodium borohydride (1.6 g.) was added. The mixture was then stirred for 2 hours and added to a mixture of N-hydrochloric acid (100 ml.) and ethyl acetate (150 ml.). The layers were separated and the ethyl acetate layer was washed with water (2 × 100 ml.), dried (MgSO$_4$) and filtered.

EXAMPLE 21

Ethyl 6-n-propylcinnolin-3-yl carboxylate m.p. 88°-9° C., was obtained by a similar method to that described in Example 20.

EXAMPLE 22

Ethyl 6-nitrocinnolin-3-yl carboxylate (150 mg.) was dissolved in ethanol (20 ml.), and 30% w/w palladium on charcoal catalyst (20 mg.) was added. The solution was shaken in an atmosphere of hydrogen at room temperature and atmospheric pressure until the theoretical uptake had taken place. The catalyst was filtered off and the ethanol solution was evaporated to dryness, yielding a yellow solid. This solid was purified by chromatography on a column of Kieselgel 60 (E. Merck, Darmstadt) using ethyl acetate as eluent. The appropriate fractions were combined and evaporated to dryness to give ethyl 6-aminocinnolin-3-yl carboxylate, m.p. 204°-6° C.

EXAMPLE 23

A solution of 5-amino-1,2,3,4-tetrazole (0.425 g.) in dry pyridine (10 ml.) was added to 6-ethylcinnolin-3-yl carbonyl chloride (1.1 g.). The resulting solution was kept at room temperature overnight, and water (50 ml.) and N-hydrochloric acid (50 ml.) were then added. The mixture was filtered, and the solid residue washed with water and crystallised from aqueous dimethylformamide to give 6-ethyl-N-(1,2,3,4-tetrazol-5-yl)cinnolin-3-yl carboxamide, m.p. over 250° C.

The acid chloride used as starting material was prepared in an analogous manner to that described in Example 26 for the preparation of 6-bromocinnolin-3-yl carbonyl chloride.

EXAMPLE 24

A mixture of glycine methyl ester hydrochloride (2.5 g.) and triethylamine (2.6 ml.) in dry methylene chloride (10 ml.) was added to a solution of 6-ethylcinnolin-3-yl carbonyl chloride (1.1 g.) in dry methylene chloride (10 ml.). The resulting solution was kept at room temperature for 5 hours, diluted with methylene chloride (80 ml.) and washed successively with N-hydrochloric acid, water, 10% w/v sodium bicarbonate solution, and water and then dried (MgSO$_4$). The solvent was evaporated and the solid residue was crystallized from aqueous ethanol to give 6-ethyl-N-(methoxycarbonylmethyl)-cinnolin-3-yl carboxamide, m.p. 135°–7° C.

EXAMPLE 25

A mixture of hydroxylamine hydrochloride (0.85 g.) and triethylamine (2 ml.) in dry methylene chloride (15 ml.) was added to a solution of 6-ethylcinnolin-3-yl carbonyl chloride (1.12 g.) in dry methylene chloride (15 ml.). The resulting solution was kept at room temperature for 3 hours, and the solvent was then evaporated in vacuo. The white solid residue was dissolved in excess N-sodium hydroxide and acidified to about pH 5 with concentrated hydrochloric acid. The resulting mixture was filtered, and the solid residue washed with cold water and crystallised from dry ethanol to give 6-ethylcinnolin-3-yl hydroxamic acid, m.p. 195=7° C.

EXAMPLE 26

A solution of 2-diethylaminoethanol (1.4 g.) in dry tetrahydrofuran (15 ml.) was added to a solution of 6-bromocinnolin-3-yl carbonyl chloride (1.07 g.) in dry tetrahydrofuran (15 ml.). The resulting solution was heated under reflux for 2 hours, and the solvent was then evaporated in vacuo. The solid residue was dissolved in water (50 ml.), the solution extracted with ethyl acetate (3 × 100 ml.), and the combined extracts dried (MgSO$_4$). The solution was evaporated to a small volume, petroleum ether (b.p. 60°–80° C.; 50 ml.) was added, the resulting mixture was filtered to give, as the solid residue, 2-diethylaminoethyl 6-bromocinnolin-3-yl carboxylate, m.p. 90°–3° C.

The acid chloride used as starting material was obtained as follows:

6-Bromocinnolin-3-yl carboxylic acid (1 g.) was added to thionyl chloride (15ml.), and the mixture was heated under reflux until gaseous evolution ceased. The excess thionyl chloride was evaporated in vacuo leaving the required acid chloride as a solid.

EXAMPLE 27

A mixture of 6-ethylcinnolin-3-yl carboxylic acid (0.606 g.) and thionyl chloride (30 ml.) was heated under reflux on a steam bath for 20 minutes. The resulting solution was evaporated under reduced pressure to give a yellow crystalline solid, to which was added a solution of phenol (1.13 g.) in dry tetrahydrofuran (20 ml.). The mixture was heated under reflux on a steam bath for 2 hours. The resulting solution was evaporated and the residue was washed by decantation with ether (2 × 50 ml.). The residual brown oil was dissolved in ethyl acetate (50 ml.) and washed successively with 5% w/v aqueous sodium bicarbonate (10 ml.) and water (2 × 10 ml.). The ethyl acetate solution was dried (MgSO$_4$), filtered and evaporated, and the residual oil was applied to the top of a silica column (30 g. Kieselgel 60). Elution with a 50% v/v mixture of ethyl acetate and petroleum ether (b.p. 60°–80° C.), and evaporation of the appropriate fractions, gave crude phenyl 6-ethylcinnolin-3-yl carboxylate. The product was recrystallised from aqueous ethanol, and then had m.p. 143°–5° C.

EXAMPLE 28

2-Ethoxyethyl 6-bromocinnolin-3-yl carboxylate, m.p. 128°–130° C., was obtained in a similar manner to that described in Example 27.

EXAMPLE 29

A solution of ethyl 6-(benzyloxycarbonylamino)-1,4-dihydrocinnolin-3-yl carboxylate in ethyl acetate (obtained as described below) was heated to reflux temperature and manganese dioxide (20 g.) was added. The mixture was heated under reflux for 30 minutes, filtered, and the filtrate evaporated in vacuo to approximately 25 ml. Petroleum ether (b.p. 60°–80° C.; 75 ml.) was added and the mixture filtered to give, as solid residue, ethyl 6-(benzyloxycarbonylamino)cinnolin-3-yl carboxylate, m.p. 205° C.

The solution used as starting material was obtained as follows:

Palladium on charcoal catalyst (30% w/w; 0.5 g.) was added to a solution of ethyl 4-hydroxy-6-nitrocinnolin-3-yl carboxylate (10 mg.) in dry pyridine (250 ml.). The mixture was shaken in an atmosphere of hydrogen at room temperature and atmospheric pressure until the desired uptake had been obtained. The mixture was then filtered through Celite and the filtrate evaporated to a volume of approx. 100 ml. Benzyl chloroformate (30 ml.) was added to the solution, and the mixture was stirred at room temperature for 16 hours. The solution was then heated at 100° C. for 1 hour, the solvent evaporated in vacuo and the residue crystallised from aqueous ethanol to give ethyl 6-(benzyloxycarbonylamino)-4-hydroxycinnolin-3-yl carboxylate, m.p. 250°–2° C.

Ethyl 6-(benzyloxycarbonylamino)-4-hydroxycinnolin-3-yl carboxylate (4g.) was suspended in thionyl chloride (90 ml.), and dimethyl formamide (0.1 ml.) was added. The suspension was warmed gently to boiling and then heated under reflux until gaseous evolution ceased. The excess thionyl chloride was evaporated in vacuo and the residue was dissolved in toluene (30 ml.). This solution was evaporated to dryness in vacuo and the residue dissolved in a mixture of ethyl acetate (200 ml.) and dimethylformamide (20 ml.). The solution was stirred and to it was added sodium borohydride (2 g.). The mixture was then stirred at room temperature for 2 hours and then added to a mixture of ethyl acetate (250 ml.) and N-hydrochloric acid (250 ml.). The mixture was separated and the organic layer washed with water and then dried (MgSO$_4$).

EXAMPLE 30

Ethyl 6-aminocinnolin-3-yl carboxylate (obtained as described below) was dissolved in acetic anhydride (25 ml.). The solution was heated at 100° C. for 16 hours and then allowed to cool to room temperature, and the resulting mixture was filtered to give, as solid residue, ethyl 6-acetylamino-cinnolin-3-yl carboxylate, m.p. 256°–8° C.

The ethyl ester used as starting material was obtained as follows:

Palladium on charcoal catalyst (30% w/w; 100 mg.) was added to a solution of ethyl 6-(benzyloxycarbonylamino)-cinnolin-3-yl carboxylate (1 g.) in dry ethanol (25 ml.). The solution was shaken in an atmosphere of hydrogen at room temperature and atmospheric pressure for 24 hours. The mixture was filtered and the filtrate evaporated in vacuo to give, as solid residue, ethyl 6-aminocinnolin-3-yl carboxylate.

EXAMPLE 31

A solution of ethyl 6-(methoxyphenyl)-1,4-dihydrocinnolin-3-yl carboxylate in ethyl acetate (obtained as described below) was heated to boiling point and manganese dioxide (15 g.) was added. The mixture was heated under reflux for 30 minutes and then filtered. The filtrate was evaporated to approx. 1 ml. in vacuo and the residue was applied to a silica column (30 g. Kieselgel 60). The column was eluted with a 50% v/v mixture of ethyl acetate and petroleum ether (b.p. 60°–80° C.). The appropriate fractions were combined and evaporated in vacuo, and the crystalline residue was recrystallised from aqueous ethanol to give ethyl 6-(methoxyphenyl)cinnolin-3-yl carboxylate m.p. 143°–5° C. (believed to be a mixture of isomers varying in the position of the methoxy radical on the phenyl substituent).

The ethyl ester used as starting material was obtained as follows:

Amyl nitrite (2 ml.) was added to a stirred suspension of ethyl 6-amino-4-hydroxycinnolin-3-yl carboxylate (2 g.) in anisole (250 ml.). The suspension was stirred and heated on a steam bath for 3 hours. The resulting solution was filtered whilst hot and the filtrate was evaporated. The residue was applied to a silica column (100 g. of Kieselgel 60) and eluted with a 10% v/v mixture of dry ethanol and chloroform. The appropriate fractions were evaporated, the residual solid [ethyl 4-hydroxy 6-(methoxyphenyl)cinnolin-3-yl carboxylate] was dissolved in thionyl chloride (50 ml.), and dimethylformamide (5 drops) added. The solution was heated under reflux until gaseous evolution ceased. The solution was then evaporated under reduced pressure, the residue dissolved in dry toluene (20 ml.), and the solution evaporated to dryness. The residue was dissolved in a mixture of dimethylformamide (2 ml.) and ethyl acetate (50 ml.), and sodium borohydride (0.5 g.) was added. The mixture was stirred for 2 hours at room temperature and then added to a mixture of N-hydrochloric acid (10 ml.) and ethyl acetate (50 ml.). The mixture was separated and the ethyl acetate layer was washed with water (3 × 20 ml.), dried (MgSO$_4$), and filtered. There was thus obtained the solution of ethyl 6-(methoxyphenyl)-1,4-dihydrocinnolin-3-yl carboxylate (believed to be a mixture of isomers varying in the position of the methoxy radical on the phenyl substituent) which was used as starting material in this Example.

EXAMPLE 32

Hydrazine hydrate (0.5 ml.) was added to a solution of ethyl 6-bromocinnolin-3-yl carboxylate (1.08 g.) in dry ethanol (25 ml.). After a short time a white solid crystallised out from the solution and this was filtered off. The solid was recrystallised from dry ethanol to give 6-bromocinnolin-3-yl carboxyhydrazide, m.p. over 250° C.

EXAMPLE 33

6-Phenylcinnolin-3-yl carboxylic acid (0.25 g.) was dissolved in concentrated sulphuric acid (1 ml.) at 0° C. in an ice bath. Concentrated nitric acid (specific gravity 1.42; 0.5 ml.) was added, and the solution was heated under reflux for 5 hours on a steam bath. The resulting pale brown solution was poured into a mixture of crushed ice and water (50 ml.), and the precipitated solid was filtered, washed with water (3 × 10 ml.) and crystallised from aqueous ethanol to give 6-(dinitrophenyl)cinnolin-3-yl carboxylic acid, m.p. 196°–8° C. (believed to be a mixture of isomers varying in the positions of the two nitro groups on the phenyl substituent).

EXAMPLE 34

Aqueous ammonia solution (specific gravity 0.88; 10 ml.) was added to 6-ethylcinnolin-3-yl carbonyl chloride (1 g.). The resulting suspension was stirred overnight at room temperature. The resulting mixture was filtered and the solid residue was crystallised from aqueous ethanol to give 6-ethylcinnolin-3-ylcarboxamide, m.p. 215°–6° C.

EXAMPLE 35

Benzyl 6-bromocinnolin-3-yl carboxylate, m.p. 171° C., was obtained in a similar manner to that described in Example 27.

EXAMPLE 36

A mixture of ethyl 6 nitrocinnolin-3-yl carboxylate (0.7 g.) and platinum oxide (100 mg.) in dry ethanol (20 ml.) acetone (20 ml.) and glacial acetic acid (0.5 ml.) was shaken in an atmosphere of hydrogen at room temperature and atmospheric pressure for 24 hours. The mixture was then heated to boiling point on a steam bath, and manganese dioxide (10 g.) was added to the boiling solution. (The above-mentioned reducing conditions resulted in the formation of relatively small amount of the 1,4-dihydrocinnoline derivative, and the manganese dioxide was used to convert this into the corresponding cinnoline derivative.) The suspension was heated under reflux for 30 minutes and then filtered through Celite. Kieselgel 60 (1 g.) was added to the filtrate, and the mixture was evaporated to dryness. The residue was placed on the top of a silica column (50 g. Kieselgel 60). Elution with ethyl acetate, evaporation of the appropriate fractions and recrystallisation from aqueous ethanol gave ethyl 6-isopropylaminocinnolin-3-yl carboxylate, m.p. 167°–8° C.

EXAMPLE 37

Methyl 6-methylcinnolin-3-yl carboxylate, m.p. 170°–2° C., was obtained in a similar manner to that described in Example 10.

EXAMPLE 38

A mixture of 6-bromocinnolin-3-yl carboxylic acid (10 g.), maize starch (65 g.), calcium phosphate (130 g.) and magnesium stearate (1 g.) was compressed, and the compressed mixture was then broken down into granules by passage through a 16-mesh screen. The resulting granules were then compressed into tablets each containing 25 mg of the active ingredient.

What we claim is:

1. A pharmaceutical composition for the treatment of a syndrome or disease initiated by an antigen-antibody reaction comprising an effective amount of a compound of the formula:

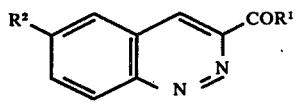
VI wherein $R^1$ stands for hydroxy, methoxy, ethoxy, 2-diethylaminoethoxy, phenoxy, hydroxyamino or 1,2,3,4-tetrazol-5-ylamino, and $R^2$ stands for ethyl, n-propyl, cyclohexyl, amino, acetylamino, phenyl, p-chlorophenyl, dinitrophenyl, chloro or bromo, or a pharmaceutically-acceptable salt thereof, and an inert pharmaceutically-acceptable diluent or carrier.

2. A compound of the formula:

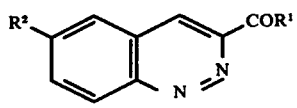
VI wherein $R^1$ stands for hydroxy, methoxy, ethoxy, 2-diethylaminoethoxy, phenoxy, hydroxyamino or 1,2,3,4-tetrazol-5-ylamino, and $R^2$ stands for ethyl, n-propyl, cyclohexyl, amino, acetylamino, phenyl, p-chlorophenyl, dinitrophenyl, chloro or bromo, or a pharmaceutically-acceptable salt thereof, but excluding ethyl 6-chlorocinnolin-3-yl carboxylate and pharmaceutically-acceptable salts thereof.

3. Composition as claimed in claim 1 which is in an orally-administrable unit dosage form.

4. A method for the treatment of a syndrome or disease initiated by an antigen-antibody reaction in a host in need of said treatment, which comprises administering to said host a functionally-effective amount of a compound of the formula I as defined in claim 1, or a pharmaceutically-acceptable salt thereof, and an inert pharmaceutically-acceptable diluent or carrier.

5. Compound as claimed in claim 2 which is 6-bromocinnolin-3-yl carboxylic acid or a pharmaceutically-acceptable salt thereof.

6. Compound as claimed in claim 2 which is 6-phenylcinnolin-3-yl carboxylic acid or a pharmaceutically-acceptable salt thereof.

7. A compound as claimed in claim 2 which is 6-chlorocinnolin-3-yl carboxylic acid or a pharmaceutically-acceptable salt thereof.

* * * * *